(12) United States Patent
Luciano et al.

(10) Patent No.: US 11,132,774 B2
(45) Date of Patent: *Sep. 28, 2021

(54) AUTOMATIC ALIGNMENT OF A CONTRAST ENHANCEMENT SYSTEM

(71) Applicant: AccuVein Inc., Medford, NY (US)

(72) Inventors: Vincent Luciano, Shoreham, NY (US); Fred Wood, Medford, NY (US)

(73) Assignee: AccuVein, Inc., Medford, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/909,093

(22) Filed: Jun. 23, 2020

(65) Prior Publication Data
US 2020/0320671 A1 Oct. 8, 2020

Related U.S. Application Data

(63) Continuation of application No. 16/741,859, filed on Jan. 14, 2020, now Pat. No. 10,713,766, which is a
(Continued)

(51) Int. Cl.
*G06T 5/00* (2006.01)
*A61B 5/00* (2006.01)
(Continued)

(52) U.S. Cl.
CPC .......... *G06T 5/009* (2013.01); *A61B 5/0059* (2013.01); *A61B 5/0082* (2013.01); *A61B 5/489* (2013.01);
(Continued)

(58) Field of Classification Search
CPC .......... A61B 2090/366; A61B 5/0059; A61B 5/0082; A61B 5/489; G06T 5/009;
(Continued)

(56) References Cited

U.S. PATENT DOCUMENTS 3,136,310 A 6/1964 Meltzer
3,349,762 A 10/1967 Kapany
(Continued)

FOREIGN PATENT DOCUMENTS

FR 2289149 5/1976
GB 1298707 2/1972
(Continued)

OTHER PUBLICATIONS

Wiklof, Chris, "Display Technology Spawns Laser Camera," LaserFocusWorld, Dec. 1, 2004, vol. 40, Issue 12, PerinWeil Corp., USA.
(Continued)

*Primary Examiner* — Thai Q Tran
*Assistant Examiner* — Stephen R Smith
(74) *Attorney, Agent, or Firm* — Thomas A. O'Rourke; Bodner & O'Rourke, LLP

(57) ABSTRACT

An apparatus and method for insuring the proper alignment of a detected vein pattern and a projected vein pattern are disclosed. The apparatus enhances the visual appearance of veins so that an error that can lead to improper patient care or injury can be avoided.

15 Claims, 3 Drawing Sheets

Related U.S. Application Data continuation of application No. 16/121,668, filed on Sep. 5, 2018, now Pat. No. 10,580,119, which is a continuation of application No. 15/665,504, filed on Aug. 1, 2017, now Pat. No. 10,096,096, which is a continuation of application No. 15/226,027, filed on Aug. 2, 2016, now Pat. No. 9,760,982, which is a continuation of application No. 14/196,172, filed on Mar. 4, 2014, now Pat. No. 9,430,819, which is a continuation of application No. 12/215,713, filed on Jun. 27, 2008, now Pat. No. 8,730,321.

(60) Provisional application No. 60/937,618, filed on Jun. 28, 2007.

(51) Int. Cl.
*H04N 5/33* (2006.01)
*H04N 9/31* (2006.01)
*A61B 90/00* (2016.01)

(52) U.S. Cl.
CPC ............. *H04N 5/33* (2013.01); *H04N 9/3176* (2013.01); *H04N 9/3185* (2013.01); *H04N 9/3194* (2013.01); *A61B 2090/366* (2016.02)

(58) Field of Classification Search
CPC ...... H04N 5/33; H04N 9/3176; H04N 9/3185; H04N 9/3194
USPC .... 348/136, 77, 162, 164, 135, 137; 345/32; 600/473; 353/1
See application file for complete search history.

(56) References Cited

U.S. PATENT DOCUMENTS

| | | | |
|---|---|---|---|
| 3,511,227 A | 5/1970 | Johnson | |
| 3,527,932 A | 9/1970 | Thomas | |
| 3,818,129 A | 6/1974 | Yamamoto | |
| 3,984,629 A | 10/1976 | Gorog | |
| 4,030,209 A | 6/1977 | Dreiding | |
| 4,057,784 A | 11/1977 | Tafoya | |
| 4,109,647 A | 8/1978 | Stern et al. | |
| 4,162,405 A | 7/1979 | Chance et al. | |
| 4,182,322 A | 1/1980 | Miller | |
| 4,185,808 A | 1/1980 | Donohoe | |
| 4,213,678 A | 7/1980 | Pomerantzeff et al. | |
| 4,265,227 A | 5/1981 | Ruge | |
| 4,312,357 A | 1/1982 | Andersson et al. | |
| 4,315,318 A | 2/1982 | Kato et al. | |
| 4,321,930 A | 3/1982 | Jobsis et al. | |
| 4,393,366 A | 7/1983 | Hill | |
| 4,495,949 A | 1/1985 | Stoller | |
| 4,502,075 A | 2/1985 | DeForest et al. | |
| 4,510,938 A | 4/1985 | Jobsis et al. | |
| 4,536,790 A | 8/1985 | Kruger et al. | |
| 4,565,968 A | 1/1986 | Macovski | |
| 4,567,896 A | 2/1986 | Barnea et al. | |
| 4,576,176 A | 3/1986 | Epstein | |
| 4,590,948 A | 3/1986 | Nilsson | |
| 4,586,190 A | 4/1986 | Tsuji | |
| 4,596,254 A | 6/1986 | Adrian et al. | |
| 4,619,249 A | 10/1986 | Landry | |
| 4,669,467 A | 6/1987 | Willett et al. | |
| 4,697,147 A | 9/1987 | Moran et al. | |
| 4,699,149 A | 10/1987 | Rice | |
| 4,703,758 A | 11/1987 | Omura | |
| 4,766,299 A | 8/1988 | Tierney | |
| 4,771,308 A | 9/1988 | Tejima et al. | |
| 4,780,919 A | 11/1988 | Harrison | |
| 4,799,103 A | 1/1989 | Muckerheide | |
| 4,817,622 A | 4/1989 | Pennypacker et al. | |
| 4,846,183 A | 7/1989 | Martin | |
| 4,861,973 A | 8/1989 | Hekekson et al. | |
| 4,862,894 A | 9/1989 | Fujii | |
| 4,899,756 A | 2/1990 | Sonek | |
| 4,901,019 A | 2/1990 | Wedeen | |
| 4,926,867 A | 5/1990 | Kanda et al. | |
| RE33,234 E | 6/1990 | Landry | |
| 4,938,205 A | 7/1990 | Nudelman | |
| 5,074,642 A | 12/1991 | Hicks | |
| 5,088,493 A | 2/1992 | Giannini et al. | |
| 5,103,497 A | 4/1992 | Hicks | |
| 5,146,923 A | 9/1992 | Dhawan | |
| 5,174,298 A | 12/1992 | Dolfi et al. | |
| 5,184,188 A | 2/1993 | Bull et al. | |
| 5,214,458 A | 5/1993 | Kanai | |
| 5,222,495 A | 6/1993 | Clarke et al. | |
| 5,261,581 A | 11/1993 | Harden, Sr. | |
| 5,293,873 A | 3/1994 | Fang | |
| 5,339,817 A | 8/1994 | Nilsson | |
| 5,371,347 A | 12/1994 | Plesko | |
| 5,406,070 A | 4/1995 | Edgar et al. | |
| 5,418,546 A | 5/1995 | Nakagakiuchi et al. | |
| 5,423,091 A | 6/1995 | Lange | |
| 5,436,655 A | 7/1995 | Hiyama et al. | |
| 5,445,157 A | 8/1995 | Adachi et al. | |
| D362,910 S | 10/1995 | Creaghan | |
| 5,485,530 A | 1/1996 | Lakowicz et al. | |
| 5,487,740 A | 1/1996 | Sulek et al. | |
| 5,494,032 A | 2/1996 | Robinson et al. | |
| 5,497,769 A | 3/1996 | Gratton et al. | |
| 5,504,316 A | 4/1996 | Bridgelall et al. | |
| 5,519,208 A | 5/1996 | Esprza et al. | |
| 5,541,820 A | 7/1996 | McLaughlin | |
| 5,542,421 A | 8/1996 | Erdman | |
| 5,598,842 A | 2/1997 | Ishihara et al. | |
| 5,603,328 A | 2/1997 | Zucker et al. | |
| 5,608,210 A * | 3/1997 | Esparza | A61B 5/0059 250/226 |
| 5,610,387 A | 3/1997 | Bard et al. | |
| 5,625,458 A | 4/1997 | Alfano et al. | |
| 5,631,976 A | 5/1997 | Bolle et al. | |
| 5,655,530 A | 8/1997 | Messerschmidt | |
| 5,678,555 A | 10/1997 | O'Connell | |
| 5,716,796 A | 2/1998 | Bull et al. | |
| 5,719,399 A | 2/1998 | Alfano et al. | |
| 5,740,801 A | 4/1998 | Branson | |
| 5,747,789 A | 5/1998 | Godik | |
| 5,756,981 A | 5/1998 | Roustaei et al. | |
| 5,758,650 A | 6/1998 | Miller et al. | |
| 5,772,593 A | 6/1998 | Hakamata | |
| 5,787,185 A | 7/1998 | Clayden | |
| 5,814,040 A | 9/1998 | Nelson et al. | |
| 5,836,877 A | 11/1998 | Zavislan | |
| 5,847,394 A | 12/1998 | Alfano et al. | |
| 5,860,967 A | 1/1999 | Zavislan et al. | |
| 5,929,443 A | 7/1999 | Alfano et al. | |
| 5,946,220 A | 8/1999 | Lemelson | |
| 5,947,906 A | 9/1999 | Dawson, Jr. et al. | |
| 5,966,204 A | 10/1999 | Abe | |
| 5,966,230 A | 10/1999 | Swartz et al. | |
| 5,969,754 A * | 10/1999 | Zeman | G09B 21/008 348/136 |
| 5,982,553 A | 11/1999 | Bloom et al. | |
| 5,988,817 A | 11/1999 | Mizushima et al. | |
| 5,995,856 A | 11/1999 | Mannheimer et al. | |
| 5,995,866 A | 11/1999 | Lemelson | |
| 6,006,126 A | 12/1999 | Cosman | |
| 6,032,070 A | 2/2000 | Flock et al. | |
| 6,056,692 A | 5/2000 | Schwartz | |
| 6,061,583 A | 5/2000 | Ishihara et al. | |
| 6,083,486 A | 7/2000 | Weissleder et al. | |
| 6,101,036 A | 8/2000 | Bloom | |
| 6,113,536 A | 9/2000 | Aboul-Hosn et al. | |
| 6,122,042 A | 9/2000 | Wunderman et al. | |
| 6,132,379 A | 10/2000 | Patacsil et al. | |
| 6,135,599 A | 10/2000 | Fang | |
| 6,141,985 A | 11/2000 | Cluzeau et al. | |
| 6,142,650 A | 11/2000 | Brown et al. | |
| 6,149,061 A | 11/2000 | Massieu et al. | |
| 6,149,644 A | 11/2000 | Xie | |
| 6,171,301 B1 | 1/2001 | Nelson et al. | |
| 6,178,340 B1 | 1/2001 | Svetliza | |

(56) References Cited

U.S. PATENT DOCUMENTS

| | | |
|---|---|---|
| 6,179,260 B1 | 1/2001 | Ohanian |
| 6,230,046 B1 | 5/2001 | Crane et al. |
| 6,240,309 B1 | 5/2001 | Yamashita et al. |
| 6,251,073 B1 | 6/2001 | Imran et al. |
| 6,263,227 B1 | 7/2001 | Boggett et al. |
| 6,272,376 B1 | 8/2001 | Marcu et al. |
| 6,301,375 B1 | 10/2001 | Choi |
| 6,305,804 B1 | 10/2001 | Rice et al. |
| 6,314,311 B1 | 11/2001 | Williams et al. |
| 6,334,850 B1 | 1/2002 | Amano et al. |
| 6,353,753 B1 | 3/2002 | Flock et al. |
| 6,424,858 B1 | 7/2002 | Williams |
| 6,436,655 B1 | 8/2002 | Bull et al. |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl et al. |
| 6,542,246 B1 | 4/2003 | Toida |
| 6,556,854 B1 | 4/2003 | Sato et al. |
| 6,556,858 B1 | 4/2003 | Zeman |
| 6,599,247 B1 | 7/2003 | Stetten |
| 6,631,286 B2 | 10/2003 | Pfeiffer et al. |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 8/2004 | Stringer et al. |
| 6,777,199 B2 | 8/2004 | Bull et al. |
| 6,782,161 B2 | 8/2004 | Barolet et al. |
| 6,845,190 B1 | 1/2005 | Smithwick et al. |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan, Jr. |
| 6,980,852 B2 | 12/2005 | Jersey-Willuhn et al. |
| 7,092,087 B2 | 8/2006 | Kumar et al. |
| 7,113,817 B1 | 9/2006 | Winchester, Jr. et al. |
| 7,158,660 B2 | 1/2007 | Gee, Jr. et al. |
| 7,158,859 B2 | 1/2007 | Wang et al. |
| 7,204,424 B2 | 4/2007 | Yavid et al. |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,280,860 B2 | 10/2007 | Ikeda et al. |
| 7,283,181 B2 | 10/2007 | Allen et al. |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts et al. |
| 7,428,997 B2 | 9/2008 | Wiklof et al. |
| 7,431,695 B1 | 10/2008 | Creaghan |
| 7,448,996 B2 | 11/2008 | Wiklof et al. |
| 7,532,746 B2 | 5/2009 | Marcotte et al. |
| 7,545,837 B2 | 6/2009 | Oka |
| 7,559,895 B2 | 7/2009 | Stetten et al. |
| 7,579,592 B2 | 8/2009 | Kaushal |
| 7,608,057 B2 | 10/2009 | Woehr et al. |
| 7,699,776 B2 | 4/2010 | Walker et al. |
| 7,708,695 B2 | 5/2010 | Akkermans et al. |
| 7,791,561 B2* | 9/2010 | Hajjar .................. G03B 21/567 345/32 |
| 7,792,334 B2 | 9/2010 | Cohen et al. |
| 7,846,103 B2 | 12/2010 | Cannon, Jr. et al. |
| 7,848,103 B2 | 12/2010 | Zhan |
| 7,904,138 B2 | 3/2011 | Goldman et al. |
| 7,904,139 B2 | 3/2011 | Chance |
| 7,925,332 B2 | 4/2011 | Crane et al. |
| 7,966,051 B2 | 6/2011 | Xie et al. |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Boccoleri et al. |
| 8,364,246 B2 | 1/2013 | Thierman |
| 8,467,855 B2 | 6/2013 | Yasui |
| 8,480,662 B2 | 7/2013 | Stolen et al. |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,537,203 B2 | 9/2013 | Seibel et al. |
| 8,548,572 B2 | 10/2013 | Crane |
| 8,630,465 B2 | 1/2014 | Wieringa et al. |
| 8,649,848 B2 | 2/2014 | Crane et al. |
| 10,580,119 B2* | 3/2020 | Luciano .................. H04N 5/33 |
| 10,713,766 B2* | 7/2020 | Luciano .................. H04N 9/3194 |
| 2001/0006426 A1 | 7/2001 | Son et al. |
| 2001/0056237 A1 | 12/2001 | Cane et al. |
| 2002/0016533 A1 | 2/2002 | Marchitto et al. |
| 2002/0111546 A1 | 8/2002 | Cook |
| 2002/0118338 A1 | 8/2002 | Kohayakawa |
| 2002/0188203 A1 | 12/2002 | Smith et al. |
| 2003/0018271 A1 | 1/2003 | Kimble |
| 2003/0037375 A1 | 2/2003 | Riley et al. |
| 2003/0052105 A1 | 3/2003 | Nagano et al. |
| 2003/0120154 A1 | 6/2003 | Sauer et al. |
| 2003/0125629 A1 | 7/2003 | Ustuner |
| 2003/0156260 A1 | 8/2003 | Putilin et al. |
| 2004/0015062 A1 | 1/2004 | Ntziachristos et al. |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0171923 A1 | 9/2004 | Kalafut et al. |
| 2004/0222301 A1 | 11/2004 | Willins et al. |
| 2004/0237051 A1 | 11/2004 | Clauson |
| 2005/0003323 A1* | 1/2005 | Katsuda .................. A61B 1/00089 433/29 |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085732 A1 | 4/2005 | Sevick-Muraca et al. |
| 2005/0085802 A1 | 4/2005 | Gruzdev et al. |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner et al. |
| 2005/0154303 A1 | 7/2005 | Walker et al. |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov et al. |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0020212 A1 | 1/2006 | Xu et al. |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle et al. |
| 2006/0103811 A1 | 5/2006 | May et al. |
| 2006/0122515 A1* | 6/2006 | Zeman .................. A61B 5/0059 600/473 |
| 2006/0129037 A1 | 6/2006 | Kaufman et al. |
| 2006/0129038 A1 | 6/2006 | Zelenchuk et al. |
| 2006/0151449 A1 | 7/2006 | Warner, Jr. et al. |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0247514 A1* | 11/2006 | Panasyuk .................. A61B 5/0059 600/410 |
| 2006/0253010 A1 | 11/2006 | Brady et al. |
| 2006/0271028 A1 | 11/2006 | Altsbuler et al. |
| 2006/0276712 A1 | 12/2006 | Stothers |

(56) References Cited

U.S. PATENT DOCUMENTS

| | | |
|---|---|---|
| 2007/0015980 A1 | 1/2007 | Numada et al. |
| 2007/0016079 A1 | 1/2007 | Freeman et al. |
| 2007/0070302 A1 | 3/2007 | Govorkov et al. |
| 2007/0115435 A1 | 5/2007 | Rosendaal |
| 2007/0129634 A1 | 6/2007 | Hickey et al. |
| 2007/0176851 A1 | 8/2007 | Willey et al. |
| 2007/0225582 A1* | 9/2007 | Diab ............... A61B 5/14551 600/336 |
| 2007/0238957 A1 | 10/2007 | Yarad |
| 2008/0039701 A1* | 2/2008 | Ali .................. A61B 5/0002 600/301 |
| 2008/0045841 A1 | 2/2008 | Wood et al. |
| 2008/0147147 A1* | 6/2008 | Griffiths ............... A61B 5/0059 607/88 |
| 2008/0194930 A1 | 8/2008 | Harris et al. |
| 2008/0214940 A1 | 9/2008 | Benaron |
| 2009/0018414 A1* | 1/2009 | Toofan ............... A61B 5/0059 600/310 |
| 2009/0028461 A1* | 1/2009 | Wieringa ............ A61B 5/0059 382/284 |
| 2009/0082629 A1 | 3/2009 | Dotan |
| 2009/0171205 A1 | 7/2009 | Kharin et al. |
| 2010/0020078 A1* | 1/2010 | Shpunt ................ G01B 11/25 345/420 |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1* | 7/2010 | Berryhill ............. A61B 5/0059 348/77 |
| 2010/0312120 A1 | 12/2010 | Meier |
| 2011/0275932 A1 | 11/2011 | Leblond et al. |
| 2013/0147916 A1 | 6/2013 | Bennett et al. |
| 2014/0039309 A1 | 2/2014 | Harris et al. |
| 2014/0046291 A1 | 2/2014 | Harris et al. |
| 2014/0194747 A1 | 7/2014 | Kruglick |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08-023501 A | 1/1996 |
| JP | 08-164123 | 6/1996 |
| JP | 2000-316866 A | 11/2000 |
| JP | 2002-328428 A | 11/2002 |
| JP | 2002-345953 A | 12/2002 |
| JP | 2004-237051 | 8/2004 |
| JP | 2004-329786 A | 11/2004 |
| JP | 2006-102360 | 4/2006 |
| KR | 2003-0020152 A | 3/2003 |
| WO | WO 1994 2237 | 10/1994 |
| WO | WO 1996 39925 | 12/1996 |
| WO | WO 1998 26583 | 6/1998 |
| WO | WO 1999 48420 | 9/1999 |
| WO | WO 2001-82786 | 11/2001 |
| WO | WO 2003-009750 | 2/2003 |
| WO | WO 2005-053773 | 6/2005 |
| WO | WO 2007-078447 | 7/2007 |

OTHER PUBLICATIONS

Nikbini, Darius, "IPMS Targets Colour Laser Projectors," Optics & Laser Europe, Mar. 1006, Isue 137, p. 11.
http://sciencegeekgirl.wordpress.com/category/science-myths/page/2/ Myth 7: Blood is Blue.
http://www.exploratorium.edu/sports/hnds_up/hands6.html "Hands Up! to Do & Notice: Getting the Feel of Your Hand".
http://www.wikihow.com/See-Block-Veins-in-Your-Hand-With-a-Flashlight "How to See Blood Veins in Your Hand With a Flashlight".

* cited by examiner

AUTOMATIC ALIGNMENT OF A CONTRAST ENHANCEMENT SYSTEM

CROSS REFERENCES TO RELATED APPLICATIONS

This application is a continuation of U.S. application Ser. No. 16/741,859, filed Jan. 14, 2020, which is a continuation of U.S. application Ser. No. 16/121,668, filed Sep. 9, 2018, now issued as U.S. Pat. No. 10,580,119, which is a continuation of U.S. application Ser. No. 15/665,504, filed Aug. 1, 2017, now issued as U.S. Pat. No. 10,096,096, which is a continuation of U.S. application Ser. No. 15/226,027, filed Aug. 2, 2016, now issued as U.S. Pat. No. 9,760,982, which is a continuation of U.S. application Ser. No. 14/196,172, filed Mar. 4, 2014, now issued as U.S. Pat. No. 9,430,819, which is a continuation of U.S. application Ser. No. 12/215,713, filed Jun. 27, 2008, now issued as U.S. Pat. No. 8,730,321, which claims priority on U.S. Provisional Application Ser. No. 60/937,618, filed Jun. 28, 2007, all disclosures of which are incorporated herein by reference.

SUMMARY OF THE INVENTION

An apparatus and method for insuring the proper alignment of a detected vein pattern and a projected vein pattern in a apparatus that enhances the visual appearance of veins so that an error that can lead to improper patient care or injury can be avoided.

BACKGROUND OF THE INVENTION

It is known in the art to use an apparatus to enhance the visual appearance of the veins and arteries in a patient to facilitate insertion of needles into those veins and arteries as well as other medical practices that require the identification of vein and artery locations. Such a system is described in U.S. Pat. Nos. 5,969,754 and 6,556,858 incorporated herein by reference as well as publication entitled "The Clinical Evaluation of Vein Contrast Enhancement". Luminetx is currently marketing such a device under the name "Veinviewer Imaging System" and information related thereto is available on their website, which is incorporated herein by reference.

The Luminetx Vein Contrast Enhancer (hereinafter referred to as LVCE) utilizes a light source for flooding the region to be enhanced with near infrared light generated by an array of LEDs. A CCD imager is then used to capture an image of the infrared light reflected off the patient. The resulting captured image is then digitally enhanced and then projected by a visible light projector onto the patient in a position that must be closely aligned with position of the captured image. The practitioner uses this projected image to determine the position in which to insert a needle. Should the image be misaligned, the patient can be injured.

DETAILED DESCRIPTION OF THE INVENTION

Figure 1:
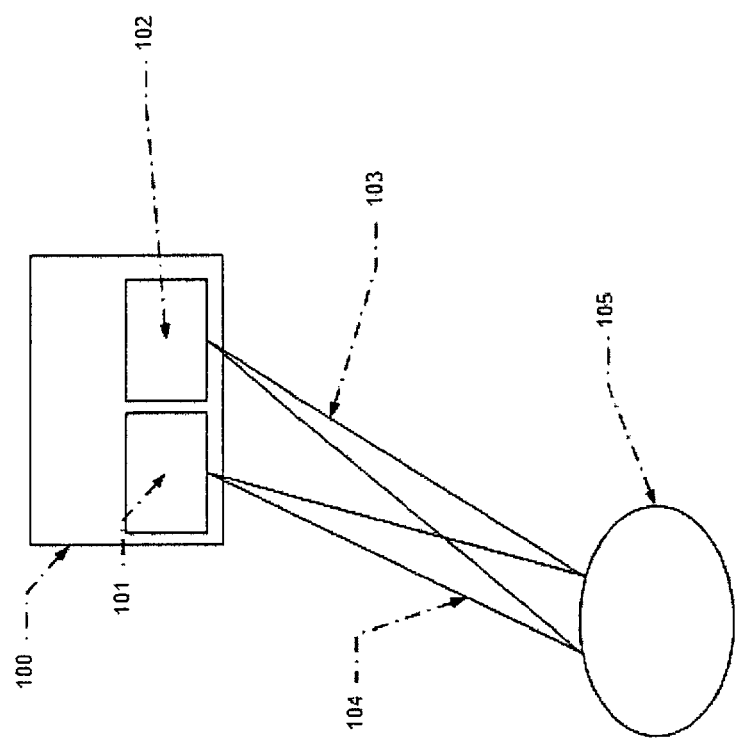
FIG. 1 shows an embodiment of a vein contrast enhancer.

As shown in FIG. 1, a typical embodiment of a vein contrast enhancer (VCE) 100 contains a camera 101 which is used to capture an image of a patient's body 105, a processing system (not shown) that enhances the image captured by the camera to highlight the positions of veins, and a projector 102 that shows an image of the enhanced vein pattern back onto the patient's body 105. Since the camera and projector are physically separate devices they reach the patient's body from different source points along different paths 103, 104. In some embodiments, the paths are made coaxial within the body of the VCE, however at some point the paths are separate since the devices (camera and projector) are physically separate devices. Since the purpose of a VCE is to allow the practitioner to insert a needle into the highlighted vein, it is critically important that the projected image and the actual vein location be aligned. Typically this alignment is done as a separate step in the use of the VCE. A card with a known pattern is placed with the viewing/projecting field of the VCE. This card has a florescent material applied to it so that when it is struck by green light, it emits infrared light that can be seen by the camera. This image is used to align the VCE.

This invention describes methods for achieving this alignment without requiring the operator to take a separate step.

Figure 2:
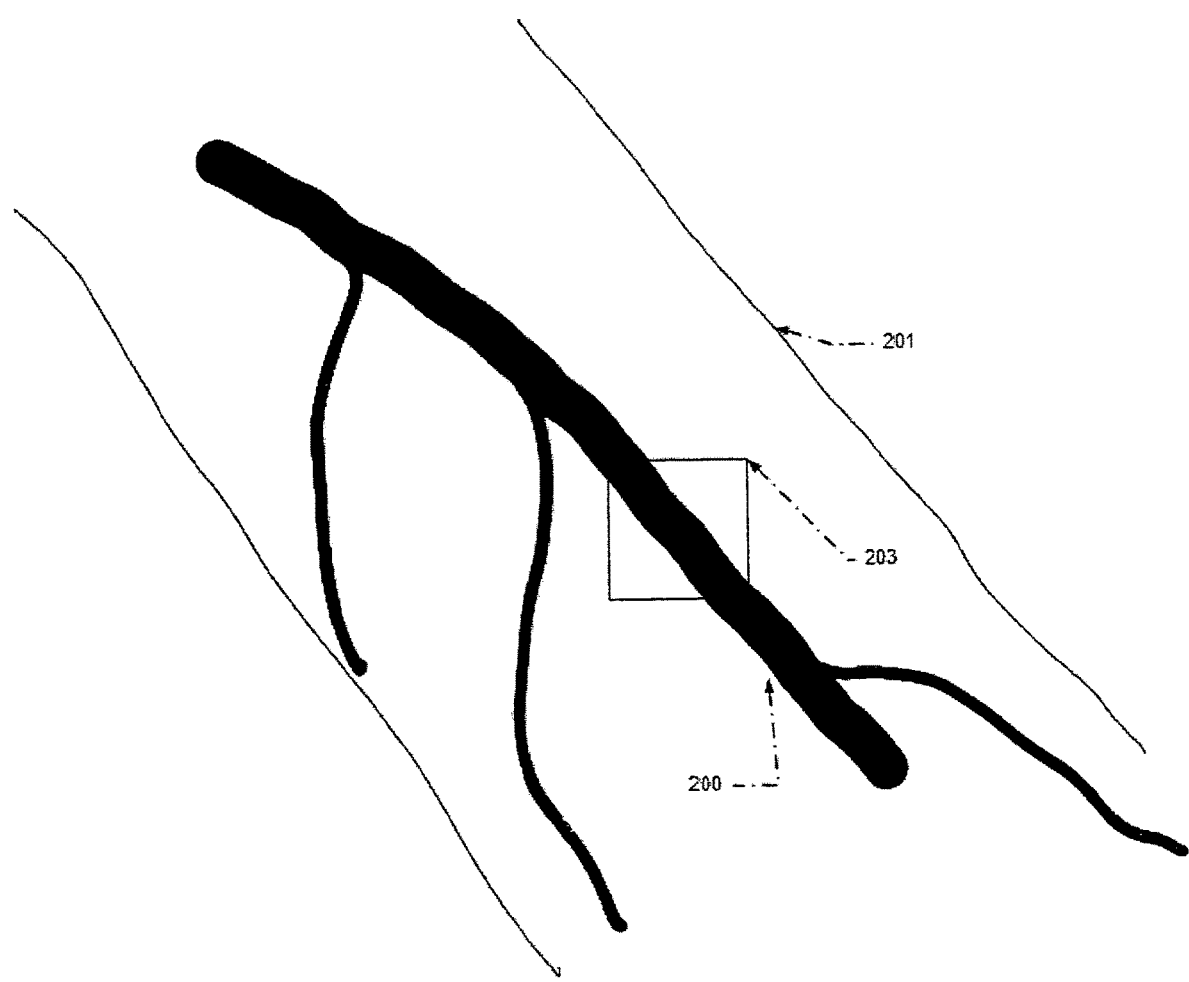
FIG. 2 is a representation of a patient's arm.
Figure 3:
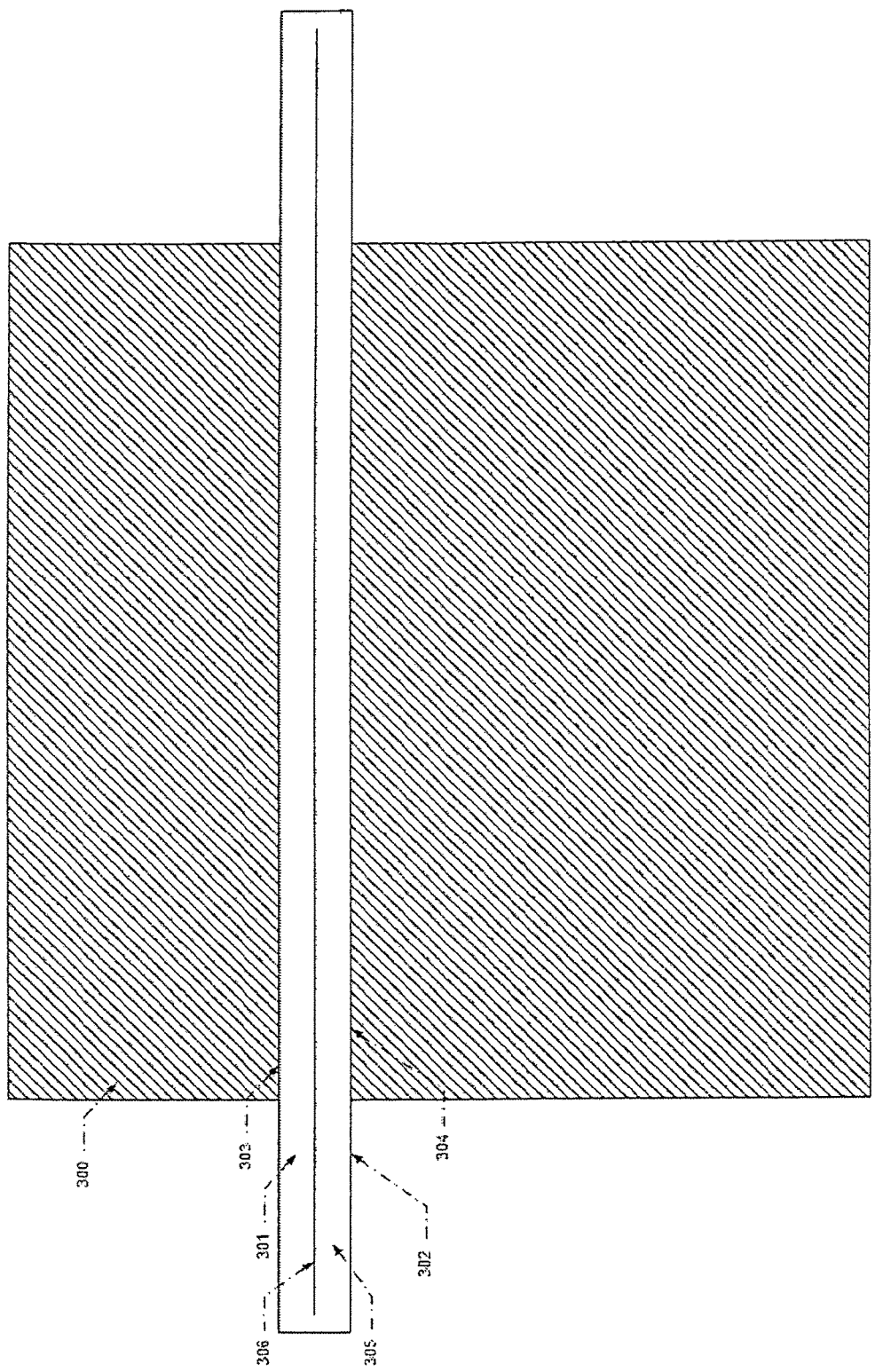
FIG. 3 shows an embodiment of a laser contrast enhancer.

Referring to FIG. 2, a representation of the patient's arm 201 is shown along with several veins. A bounding box is shown around a single vein 200. In FIG. 3, a schematic representation of the bounded area of the single vein is shown 305. Typically, the enhancement image will light up the area around the vein and will be dark on the vein. When properly aligned, the bright part of the image 300 will have edges that properly align with the edges of the vein 303, 304. As previously described, the VCE will typically have an alignment mode wherein a known pattern, typically presented on an alignment card, will be placed in front of the VCE and an alignment will be performed. This alignment can either be automatically performed by the VCE or manually performed by the operator. The weakness of this kind of implementation is that it relies on the expectation that the alignment will be maintained over time. If the alignment should shift, patient injury can occur.

In a typical VCE, an infrared light source and a camera that is sensitive only to infrared light is used to detect the vein position. Furthermore, the projected image is often green in color to insure that the light from the projector is ignored since the camera is sensitive only to light near the infrared region. This selectivity can be implemented either with filters or with selectively sensitive camera elements.

Referring back to FIG. 3, in a typical LCE, the camera, by design, is blind to the projected light. In our invention, the camera is by design, able to selectively see the projected light. In a preferred embodiment, a multi-color capable projector is used. As usual, green is used to fill the area outside of the vein 300. That green projection goes to the edges of the vein position 303, 304 and the vein area itself is left dark. A camera that is sensitive to red and infrared light is used in this embodiment. In addition to the green fill, red lines are drawn at the edges of the veins 303, 304. Since the camera can see these red lines, the image enhancement software can look to see if the red lines are at the proper position and if needed automatic alignment can be performed. An alternative embodiment would be to paint a red line 306 down the middle of the vein position. An alternative embodiment would be to paint some pattern of red light over a desired portion of the vein.

Typically the cameras used in an LCE are monochrome and unable to discriminate between light of different wavelengths. Depending on the sensitivity of the camera and the brightness of the projector compared to the infrared flood lighting provided by the LCE, various techniques can be used to aid the camera in the detection of the red lines. One method is to simply look for the brightening caused by the addition of the red lines to the reflected infrared light. A second method is to periodically turn off the infrared lighting such that only ambient infrared and the projected red are seen by the camera. This can make it easier for the system to detect the red lines.

Although we've described the invention using red and green lights, various combinations of colors can be used. Red and infrared light are known in the art to be useful for vein detection. Any combinations of colors of shorter wavelengths can be used for projection and alignment images as long as the camera selected is properly selected or filtered to achieve the desired discrimination between wavelengths. Furthermore, while discrimination between projection, detection and alignment signals in the preferred embodiment has been described using different wavelengths to separate the signals, in an embodiment with less freedom of projected color, time division can be used where the projected image is shown most of the time and the alignment image is shown interspersed on a lower duty cycle basis. Properly implemented, the alignment image will be quite visible to the VCE's camera, but invisible to the operator of the VCE.

Projectors in VCEs can be either monochrome (e.g., projecting green only) or multicolor (e.g., projecting RGB). The advantage of a monochrome implementation is that since an array of single color LEDs can be used in place of white bulbs and a color wheel typically found in a multicolor projector the system can be of lower cost, generate less heat and have higher reliability. In each an embodiment, the time division scheme describe above would be appropriate. In this monochrome configuration, an alternative embodiment would be to add a smaller array of a second color of LEDs (i.e., red). This alignment array can be smaller than the projection array in that it doesn't need to be visible to the operator, just to the camera. The projection LEDs and the alignment LEDs could then be time multiplexed as previously described.

We claim:

1. A vein imaging system comprising:
   a light source to illuminate a field of view with a first wavelength of light comprising an infrared wavelength, to create an image contrast of one or more veins formed by differential amounts of absorption and reflection of said first wavelength of light by the one or more veins and surrounding tissue in the field of view;
   an alignment card comprising a pattern formed of a material that emits a second wavelength of light when exposed to a third wavelength of light;
   an imager configured to capture said image contrast of the one or more veins at said first wavelength of light;
   a projector configured to receive and to project said captured image contrast onto the field of view using said third wavelength of light;
   wherein said imager is further configured to capture said second wavelength of light emitted by said pattern when positioned in the field of view, and to capture said third wavelength of light reflected from said pattern, said imager being further configured to distinguish said third wavelength of light reflected by said pattern, from said second wavelength of light emitted by said pattern; and
   an image processor configured to align said projection of said image contrast with said image contrast formed by the differential absorption and reflection, using said distinction between said captured reflection of said pattern at said third wavelength of light, and said captured emission from said pattern at said second wavelength of light.

2. The vein imaging system according to claim 1 wherein said pattern comprises a fluorescent material.

3. The system according to claim 1 wherein said pattern comprises a known pattern.

4. The vein imaging system according to claim 1 wherein said third wavelength of light comprises a human visible wavelength of light.

5. The vein imaging system according to claim 1 wherein said third wavelength of light comprises a green wavelength of light.

6. The vein imaging system according to claim 5 wherein said second wavelength of light comprises a red wavelength of light.

7. The vein imaging system according to claim 6 wherein said green wavelength of light of said projected image contrast is projected onto the field of view outside of the one or more veins.

8. The vein imaging system according to claim 1 wherein said third wavelength of light and said infrared first wavelength of light are alternately projected and illuminated, respectively.

9. The vein imaging system according to claim 8 wherein said third wavelength of light is projected at a higher duty cycle than said illumination with said infrared wavelength.

10. The vein imaging system according to claim 1 wherein said projector is further configured to project a line along the middle of each of the one or more veins.

11. A vein imaging system comprising: a light source to illuminate a field of view with a first wavelength of light comprising an infrared wavelength, to create an image contrast of one or more veins formed by differential amounts of absorption and reflection of said first wavelength of light by the one or more veins and surrounding tissue in the field of view; an imager configured to capture said image contrast of the one or more veins at said first wavelength of light; a projector configured to receive said captured image contrast and to project lines at an edge of each of the one or more veins in said captured image contrast with a second wavelength of light, said second wavelength of light comprising a visible wavelength; wherein said imager is further configured to capture said projected edge lines for the one or more veins at said second wavelength of light reflected from the field of view, and to distinguish said captured edge lines of the one or more veins at said second wavelength of light from the edge of each of the one or more veins in said contrasted image at said first wavelength of light; and an image processor configured to align said projection of said edge lines for each of the one or more veins with said reflected edge lines of the one or more veins.

12. The vein imaging system according to claim 11 wherein said visible second wavelength of light and said infrared first wavelength of light are alternately projected and illuminated.

13. The vein imaging system according to claim 11 wherein said projected visible third wavelength of light is projected at a higher duty cycle than said illumination of said infrared wavelength.

14. The vein imaging system according to claim 11 wherein said visible second wavelength of light comprises a green wavelength of light.

15. The vein imaging system according to claim 11 wherein said projector is further configured to project a line along the middle of each of the one or more veins.

* * * * *